United States Patent [19]

Beck et al.

[11] 4,140,857
[45] Feb. 20, 1979

[54] PROCESS FOR THE PREPARATION OF 2,4,5-TRICHLOROPYRIMIDINE

[75] Inventors: Gunther Beck; Helmut Heitzer, both of Leverkusen, Fed. Rep. of Germany

[73] Assignee: Bayer Aktiengesellschaft, Leverkusen, Fed. Rep. of Germany

[21] Appl. No.: 868,727

[22] Filed: Jan. 11, 1978

[30] Foreign Application Priority Data

Jan. 18, 1977 [DE] Fed. Rep. of Germany ....... 2701797

[51] Int. Cl.² ........................................... C07D 239/02
[52] U.S. Cl. .................................................... 544/334
[58] Field of Search .................... 260/251 R; 544/334

[56] References Cited

U.S. PATENT DOCUMENTS

| 3,714,164 | 1/1973 | Steffan | 260/251R |
| 3,920,649 | 11/1975 | Beck et al. | 260/251 R |
| 4,026,892 | 5/1977 | Beck et al. | 260/251 R |

Primary Examiner—Nicholas S. Rizzo
Attorney, Agent, or Firm—Plumley and Tyner

[57] ABSTRACT

Process for the preparation of 2,4,5-trichloropyrimidine, characterized in that compounds of the formula

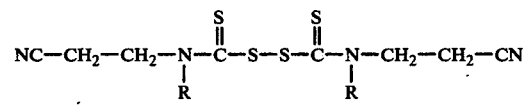

wherein
R = a radical which can be split off under the reaction conditions are reacted with more than 7 and less than 13 mols of chlorine, in particular 11 mols of chlorine, at temperatures from 0–40° C. and the reaction mixture is then subsequently heated in the absence of chlorine to temperatures from about 100–150° C., in particular 110–140° C.

6 Claims, No Drawings

PROCESS FOR THE PREPARATION OF 2,4,5-TRICHLOROPYRIMIDINE

The present invention relates to a new process for the preparation of 2,4,5-trichloropyrimidine.

The process is characterised in that N,N'-bis-(2-cyanoethyl)-thioperoxydicarboxylic acid diamides of the formula

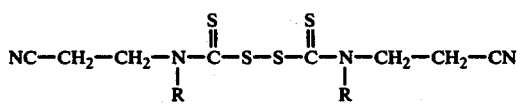

wherein

R denotes a radical which can be split off under the reaction conditions, optionally mixed with an inert diluent, are reacted with more than 7 and less than 13 mols of chlorine, in particular 11 mols of chlorine, at temperatures from 0–40° C., preferably 30–40° C., and the reaction mixture is then subsequently heated in the absence of chlorine to temperatures from about 100 to 150° C., in particular 110–140° C.

In a preferred embodiment, the chlorination is carried out at temperatures from about 20° C. to about 40° C. until the exothermic reaction has ended and the reaction mixture is then subsequently heated in the absence of chlorine to temperatures from 110 to 140° C. A further preferred embodiment consists in initially reacting the compounds of the formula (I) with hydrogen chloride, before the actual chlorination reaction, at 0–50° C., preferably 20–40° C., until the exothermic reaction has ended.

Suitable radicals R which can be split off under the reaction conditions are, in particular, lower alkyl, preferably $C_1$-$C_4$-alkyl, such as methyl, ethyl, propyl, or butyl, and furthermore lower, in particular $C_2$-$C_4$, alkenyl, such as allyl, it being possible for these groups also to be substituted, for example by chlorine, $C_1$-$C_4$-alkoxy or optionally substituted phenyl.

Suitable radicals of this type are, for example, chloroethyl, methoxyethyl, benzyl, phenylethyl, chloropropyl, dichloropropyl and methoxypropyl.

Methyl is particularly preferred.

In addition to chlorine, all the customary chlorinating agents which can split off chlorine under the reaction conditions are, of course, suitable.

Examples which may be mentioned are: sulphur dichloride, sulphuryl chloride and phosphorus pentachloride.

Only some of the starting compounds of the formula (I) are known. However, they can be easily prepared according to the instructions in the literature (for example Acta Chim. Acad. Sci. Hung. 51, 319 (1967)), by initially reacting, according to the following equation

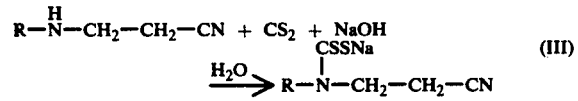

cyanoethylated amines (II) in which

R has the abovementioned meaning, with carbon disulphide in aqueous sodium hydroxide solution to give the dithiocarbamates of the formula (III), which are then converted into the disulphides of the formula (I) by oxidation, for example with hydrogen peroxide in sulphuric acid according to the following equation:

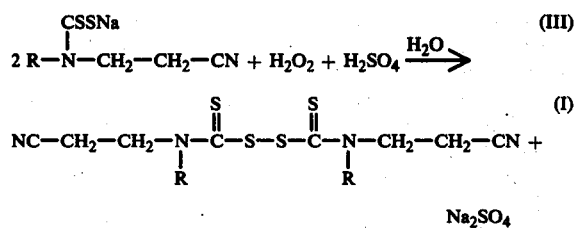

The cyanoethylated amines (II) are obtained, for example, according to the following equation

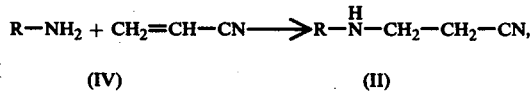

by subjecting primary amines (IV), in which

R has the abovementioned meaning, to an addition reaction with acrylonitrile.

(Compare, for example, J. Am. Chem. Soc. 66, 725 (1944), J. Am. Chem. Soc. 68, 1,217 (1946), J. Am. Chem. Soc. 78, 2,573 (1956) and J. Heterocyclic Chem. 1, 260 (1964).

N,N'-Bis-(2-cyanoethyl)-thioperoxydicarboxylic acid diamides of the formula (I) which are suitable for the process according to the invention are, for example: N,N'-bis-(2-cyanoethyl)-N,N'-dimethyl-thioperoxydicarboxylic acid diamide, N,N'-bis-(2-cyanoethyl)-N,N-diethyl-thioperoxydicarboxylic acid diamide, N,N'-bis-(2-cyanoethyl)-N,N'-bis-(2-chloroethyl)thioperoxydicarboxylic acid diamide, N,N'-bis-(2-cyanoethyl)-N,N'-bis-(2-methoxyethyl)-thioperoxydicarboxylic acid diamide, N,N'-bis-(2-cyanoethyl)-N,N'-dipropyl-thioperoxydicarboxylic acid diamide, N,N'-bis-(2-cyanoethyl)-N,N'-diallyl-thioperoxydicarboxylic acid diamide, N,N'-bis-(2-cyanoethyl)-N,N'-bis-(3-methoxypropyl)-thioperoxydicarboxylic acid diamide, N,N'-bis-(2-cyanoethyl)-N,N'-bis(2,3-dichloropropyl)-thioperoxydicarboxylic acid diamide, N,N'-bis-(2-cyanoethyl)-N,N'-dibutyl-thioperoxydicarboxylic acid diamide, N,N'-bis-(2-cyanoethyl)-N,N'-dibenzyl-thioperoxydicarboxylic acid diamide and N,N'-bis(2-cyanoethyl)-N,N'-diphenylethyl-thioperoxydicarboxylic acid diamide.

Diluents which are inert under the reaction conditions are all the solvents which are resistant to chlorine, for example chlorinated aliphatic and aromatic hydrocarbons, such as methylene chloride, chloroform, carbon tetrachloride, 1,1,2,2-tetrachloroethane, tetrachloroethylene, 1,1,2,3,3-pentachloropropane, hexachlorocyclopentadiene, octachlorocyclopentene and 1,2,4-trichlorobenzene, chlorinated pyrimidines and phosphorus oxychloride. In general, 0.5 to 20, preferably 1 to 10, parts by volume of diluent are used per part by weight of (I).

In the case where the chlorinating agent is a liquid under the reaction conditions, such as, for example, sulphur dichloride or sulphuryl chloride, the additional use of an inert solvent can be dispensed with.

When chlorine is used as the chlorinating agent, the reaction initially proceeds strongly exothermically. The reaction is therefore appropriately not carried out with an excess of chlorine, in particular in the case of larger batches, until the exothermic reaction has subsided. After the first strongly exothermic chlorination phase has subsided, the chlorination is appropriately carried out with an excess of chlorine (recognisable from the greenish colour of the chlorination off-gas), in order to complete the reaction as rapidly as possible.

When other chlorinating agents are used, for example SCl₂, it can be appropriate to employ an excess from the beginning.

In detail, the process is carried out by initially mixing a N,N'-bis-(2-cyanoethyl)-thioperoxydicarboxylic acid diamide of the formula (I), in particular N,N'-bis-(2-cyanoethyl)-N,N'-dimethyl-thioperoxydicarboxylic acid diamide, with one of the diluents mentioned, for example chloroform, at room temperature and then adding the chlorinating agent. In this procedure, the external cooling and metering of the chlorinating agent are matched with one another so that the initially strongly exothermic reaction does not become too vigorous and the temperature does not exceed 40° C.

If hydrogen chloride gas is passed in, before the chlorination reaction, at about 20–30° C., whilst cooling, until the exothermic reaction has ended, the subsequent chlorination reaction proceeds a little less vigorously and can therefore be handled more conveniently.

After the passing in of HCl has ended, the chlorination reaction is preferably carried out at about 30–40° C. until the exothermic reaction has subsided completely. Chlorine which is still dissolved in the reaction mixture and the sulphur chloride formed by the chlorination reaction are then stripped off in vacuo below 40° C. and the residue is heated, either still in vacuo or under normal pressure, with the exclusion of moisture, up to about 120–130° C., whereupon 2,4,5-trichloropyrimidine is formed. The 2,4,5-trichloropyrimidine is separated off by distillation, for example with the aid of a Ag-mirrored packed column of about 1 m in length. It can be easily obtained in a purity of over 99%.

If the reaction is carried out in the absence of an inert diluent with a chlorinating agent which is liquid under the reaction conditions, such as sulphur dichloride, it is advisable to initially introduce the latter and to meter in the starting material (I) at 30–40° C. in portions.

2,4,5-Trichloropyrimidine can be converted into tetrachloropyrimidine by gas phase chlorination (British Patent Specification No. 1,201,228). Tetrachloropyrimidine is a suitable reactive component for the preparation of reactive dyestuffs (compare, for example Belgian Patent Specification No. 578,933). Moreover, 2,4,5-trichloropyrimidine possesses fungicidal and sporicidal properties (compare U.S. Pat. No. 3,227,612).

EXAMPLE

A strong stream of HCl is passed over a stirred solution of 100 g (0.314 mol) of N,N'-bis-(2-cyanoethyl)-N,N'-dimethyl-thioperoxydicarboxylic acid diamide in 500 ml of pure chloroform between 20 and 30° C., whilst cooling, until the exothermic reaction has ended (time required about 15 minutes). A stream of chlorine is then passed in between 30 and 40° C., whilst cooling until the exothermic reaction has ended (time required about 45 minutes). Chloroform and the sulphur chloride formed during the reaction are now stripped off via a bridge under a water pump vacuum and the solid residue is heated further in vacuo to 120–130° C. in the course of about one hour. During this procedure, the residue melts, splitting off methyl chloride and simultaneously forming 2,4,5-trichloropyrimidine, some of which distils off via the bridge. For complete distillation, the bath temperature is then increased to 180° C. The entire distillate is now coarsely fractionated by taking off chloroform and sulphur dichloride at 760 mm Hg up to a bath temperature of 100° C. The residue which remains (101 g) consists, according to the gas chromatogram, to the extent of 90% of 2,4,5-trichloropyrimidine. This corresponds to a yield of 79% of theory. By rectification on a Ag-mirrored packed column of 1 m in length, 2,4,5-trichloropyrimidine is obtained at a boiling point₁₂ of 94–96° C. in a purity of over 99%.

We claim:

1. Process for the preparation of 2,4,5-trichloropyrimidine, characterized in that compounds of the formula

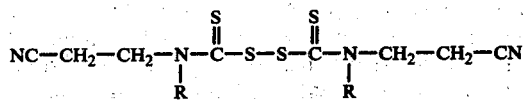

wherein
R is $C_1$-$C_4$-alkyl or $C_2$-$C_4$-alkenyl which are unsubstituted or substituted with chloro, $C_1$-$C_4$-alkoxy, or phenyl, are reacted with more than 7 and less than 13 mols of chlorine at temperatures from 0° C. to 40° C. and the reaction mixture is then subsequently heated in the absence of chlorine to temperatures from about 100° C. to 150° C.

2. Process according to claim 1, characterised in that the chlorination is carried out at temperatures from about 20° C. to about 40° C. until the exothermic reaction has ended and the reaction mixture is then subsequently heated in the absence of chlorine to temperatures from 110–140° C.

3. Process according to claim 1, characterised in that R = $C_1$-$C_4$-alkyl.

4. Process of claim 3, wherein R is methyl.

5. Process of claim 1, wherein said compounds are reacted with 11 mols of chlorine.

6. Process of claim 5, wherein the reaction mixture is subsequently heated in the absence of chlorine at temperatures from about 110° C. to 140° C.

* * * * *